US009969775B2

(12) United States Patent
Wisniewski et al.

(10) Patent No.: US 9,969,775 B2
(45) Date of Patent: May 15, 2018

(54) CGRP ANTAGONIST PEPTIDES

(71) Applicant: Ferring B.V., Hoofddorp (NL)

(72) Inventors: Kazimierz Wisniewski, San Diego, CA (US); Guangcheng Jiang, San Diego, CA (US); Aleksandr K. Rabinovich, La Jolla, CA (US); Javier J. Sueiras-Diaz, La Jolla, CA (US)

(73) Assignee: Ferring B.V., Hoofddorp (NL)

( * ) Notice: Subject to any disclaimer, the term of this patent is extended or adjusted under 35 U.S.C. 154(b) by 0 days. days.

(21) Appl. No.: 15/540,460

(22) PCT Filed: Jan. 6, 2016

(86) PCT No.: PCT/EP2016/050110
§ 371 (c)(1),
(2) Date: Jun. 28, 2017

(87) PCT Pub. No.: WO2016/110499
PCT Pub. Date: Jul. 14, 2016

(65) Prior Publication Data
US 2018/0002378 A1    Jan. 4, 2018

Related U.S. Application Data

(60) Provisional application No. 62/100,371, filed on Jan. 6, 2015.

(51) Int. Cl.
*A61K 38/00*    (2006.01)
*C07K 7/06*     (2006.01)

(52) U.S. Cl.
CPC ............... *C07K 7/06* (2013.01); *A61K 38/00* (2013.01)

(58) Field of Classification Search
None
See application file for complete search history.

(56) References Cited

FOREIGN PATENT DOCUMENTS

WO    2005095383 A1    10/2005
WO    2013112912 A1    8/2013

OTHER PUBLICATIONS

Bisello, et al., "Parathyroid Hormone-Receptor Interactions Identified Directly by Photocross-linking and Molecular Modeling," J. Biol. Chem, 1998, 273: 22498-22505.

International Search Report and Written Opinion in International Application No. PCT/EP2016/050110, dated Mar. 23, 2016, 7 pages.
Merrifield, "Solid Phase Peptide Synthesis. I. The Synthesis of a Tetrapeptide," J. Am. Chem. Soc, 1963, 85: 2149-2154.
Yan et al., "Discovery of potent, cyclic calcitonin gene-related peptide receptor antagonists." Journal of Peptide Science, May 2011, 17: 383-386.
Ian M. Bell, Calcitonin Gene-Related Peptide Receptor Antagonists: New Therapeutic Agents for Migraine; J. Med. Chem., 2014, 57, pp. 7838-7858.
F.A. Russell, et al., Calcitonin Gene-Related Peptide: Physiology and Pathophysiology; Physiol Rev 94, 2014, pp. 1099-1142.
Jakob Moller Hansen, et al., Calcitonin Gene-Related Peptide Triggers Migraine-like Attacks in Patients With Migraine With Aura; Cephalalgia 30(10), pp. 1179-1186.
Manja Lang, et al., Identification of the Key Residue of Calcitonin Gene Related Peptide (CGRP) 27-37 to Obtain Antagonists with Picomolar Affinity at the CGRP Receptor; J;. Med. Chem. 2006, 49, pp. 616-624.
Marcelo E. Bigal, M.D., et al.; Calcitonin Gene-Related Peptide (CGRP) and Migraine Current Understanding and State of Development; American Headache Society, 2013, pp. 1230-1244.
Jakob M. Hansen, et al., Calcitonin Gene-Related Peptide Does Not Cause Migraine Attacks in Patients With Familial Hemiplegic Migraine; American Headache Society, 2011, pp. 544-553.
LH Lassen, et al., CGRP May Play a Causative Role in Migraine; Blackwell Science Ltd. Cephalalgia, 2002, 22, pp. 54-61.

*Primary Examiner* — Jeanette M Lieb
(74) *Attorney, Agent, or Firm* — Fish & Richardson P.C.

(57) ABSTRACT

This disclosure relates to compounds of formula (I) or a pharmaceutically acceptable salt thereof:

in which m, p, A, $Ar^1$, $Ar^2$, $Ar^3$, $R^1$, $R^2$, and $R^3$ are defined in the specification. The compounds of formula (I) can be used as CGRP antagonists and can be used to treat migraine.

17 Claims, No Drawings

CGRP ANTAGONIST PEPTIDES

CROSS REFERENCE TO PRIOR APPLICATIONS

This is a U.S. National Phase application under 35 U.S.C. § 371 of International Patent Application No. PCT/EP2016/050110, filed Jan. 6, 2016, which claims priority to U.S. Provisional Application No. 62/100,371, filed Jan. 6, 2015. The parent applications are hereby incorporated by reference in their entirety.

TECHNICAL FIELD

This disclosure relates to CGRP antagonist peptides, as well as related compositions and methods.

BACKGROUND

Migraine is a debilitating condition characterized by recurrent attacks of often severe throbbing headache, typically together with nausea and sensitivity to light and sound. Migraines are frequently preceded by a focal neurological symptom called an aura. Current standard of care for treating migraine is the use of the triptan class of drugs. However, approximately 30% of patients do not find relief from triptans. In addition, triptans are contraindicated in migraneurs with high risk for cardiovascular diseases (e.g., diabetes, obesity, and hypercholesterolemia). Thus, there remains a need for new therapeutic paradigms for the treatment of migraine.

Calcitonin gene related peptide (CGRP) is a 37 amino acid peptide, resulting from alternative splicing of the calcitonin gene. CGRP is implicated in many physiological and pathophysiological conditions. It was discovered that truncated peptides (e.g., CGRP(8-37) or CGRP(27-37)) could act as antagonists at the CGRP receptor. These peptides were useful as research tools, but such peptides were not pursued in clinical trials. Drug discovery efforts focusing on non-peptidic small molecules yielded several compounds that advanced to clinical development, such as olcegepant and telcagepant. Despite apparent effectiveness in treating migraine, these programs were all stopped, mostly due to concerns of liver toxicity. More recently, drug development efforts targeting the CGRP pathway for migraine have refocused on monoclonal antibodies against CGRP or its receptor.

The CGRP receptor is the seven transmembrane CLR (calcitonin like receptor) in complex with RAMP1 (Receptor Activity Modulating Peptide 1). In addition to CGRP receptor, CGRP also activates the adrenomedullin (AM) receptors AM1 and AM2 (CLR+RAMP2 and CLR+RAMP3, respectively) at higher concentrations. The AM receptors are thought to have an effect on reproduction; cardiovascular and kidney function; inflammation and other conditions. A selective CGRP-R antagonist with reduced activity at the AM receptors would reduce risk of adverse events due to disruption of AM signaling.

SUMMARY

In one aspect, this disclosure features a compound of formula (I) or a salt thereof:

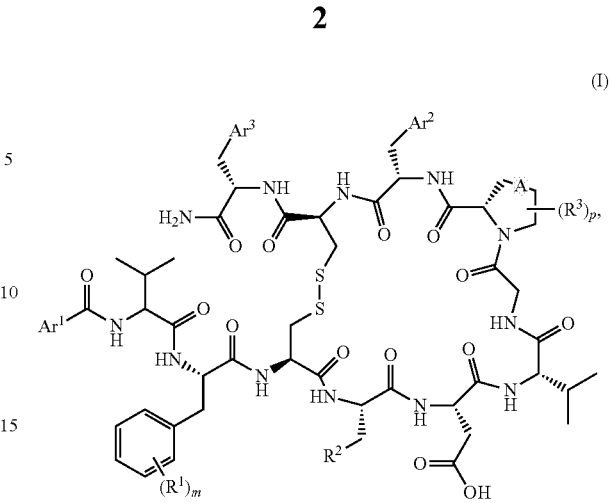

(I)

in which m is 0, 1, 2, 3, 4, or 5; p is 0, 1, 2, or 3; A is single or double carbon-carbon bond; $Ar^1$ is aryl or 5- or 6-membered heteroaryl, each of which is optionally substituted with one or more substituents, each substituent independently being halogen, nitro, $C_1$-$C_4$ alkyl, $C_1$-$C_4$ hydroxyalkyl, $OR_a$, or $N(R_aR_{a'})$, in which each $R_a$, independently, is H or $C_1$-$C_4$ alkyl and each $R_{a'}$, independently, is H or $C_1$-$C_4$ alkyl; $Ar^2$ is aryl or 5- or 6-membered heteroaryl, each of which is optionally substituted with one or more substituents, each substituent independently being halogen, cyano, nitro, $C_1$-$C_4$ alkyl, $C_1$-$C_4$ aminoalkyl, $C_1$-$C_4$ hydroxyalkyl, $OR_b$, $N(R_bR_{b'})$, $C(O)$—$N(R_bR_{b'})$, or NH—C(O)—$N(R_bR_{b'})$, in which each $R_b$, independently, is H or $C_1$-$C_4$ alkyl and each $R_{b'}$, independently, is H or $C_1$-$C_4$ alkyl; $Ar^3$ is aryl or 5- or 6-membered heteroaryl, each of which is optionally substituted with one or more substituents, each substituent independently being halogen, $C_1$-$C_4$ alkyl, $C_1$-$C_4$ hydroxyalkyl, $OR_c$, or $N(R_cR_{c'})$, in which each $R_c$, independently, is H or $C_1$-$C_4$ alkyl and each $R_{c'}$, independently, is H or $C_1$-$C_4$ alkyl; each $R^1$, independently, is $C_1$-$C_4$ alkyl, $C_1$-$C_4$ aminoalkyl, $C_1$-$C_4$ hydroxyalkyl, $OR_d$, or $C(O)$—$N(R_dR_{d'})$, in which each $R_d$, independently, is H or $C_1$-$C_4$ alkyl and each $R_{d'}$, independently, is H or $C_1$-$C_4$ alkyl; $R^2$ is —$(CH_2)_n$—R, in which n is 0, 1, 2, or 3 and R is substituted or unsubstituted guanidino, aminoacyl, $C_1$-$C_4$ alkylaminoacyl, $OR_e$, $N(R_eR_{e'})$, NH—C(O)—CH($NH_2$)—$(CH_2)_4$—$N(R_eR_{e'})$, NH—C(O)—$CH_2$—(OCH$_2$CH$_2$)$_2$—$N(R_eR_{e'})$, or 5-membered heterocycloalkyl optionally substituted with $C_1$-$C_4$ alkyl or $N(R_eR_{e'})$, in which each $R_e$, independently, is H or $C_1$-$C_4$ alkyl and each $R_{e'}$, independently, is H or $C_1$-$C_4$ alkyl; and each $R^3$, independently, is halogen, $C_1$-$C_4$ alkyl, or $OR_f$, in which each $R_f$, independently, is H or $C_1$-$C_4$ alkyl; with the provisos that, when n is 0, R is not amino or guanidino and that, when the amino acid residue bonded to $Ar^1C(O)$ is L-Val, $Ar^1$ is not unsubstituted phenyl.

In another aspect, this disclosure features a pharmaceutical composition that includes a compound of formula (I) described herein and a pharmaceutically acceptable carrier.

In still another aspect, this disclosure features a method of treating migraine that includes administering to a patient in need thereof an effective amount of the pharmaceutical composition described herein.

Other features, objects, and advantages will be apparent from the description and the claims.

DETAILED DESCRIPTION

This disclosure generally relates to CGRP antagonist peptides and their use for treating migraine. In particular, this disclosure is based on the unexpected discovery that certain peptides are CGRP antagonists that exhibit improved potency for CGRP receptor, and can be used effectively for treating migraine. In certain embodiments, the CGRP antagonist peptides are more selective for CGRP receptor vs. AM2 receptor. In certain embodiments, the CGRP antagonist peptides have improved solubility. In certain embodiments, the CGRP antagonist peptides have improved bioavailability.

In some embodiments, the CGRP antagonist peptides described herein are those of formula (I) or a pharmaceutically acceptable salt thereof:

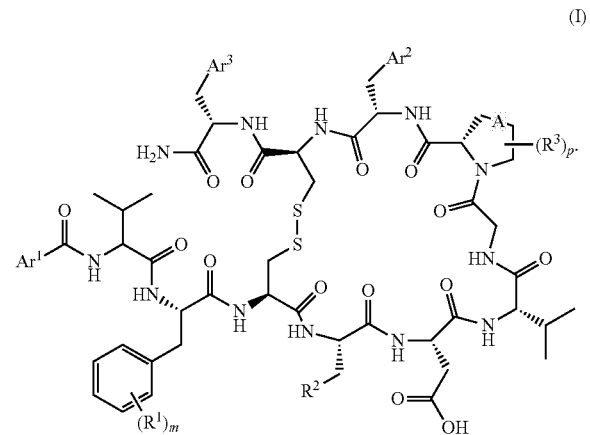

(I)

In formula (I), m is 0, 1, 2, 3, 4, or 5; p is 0, 1, 2, or 3; A is single or double carbon-carbon bond; $Ar^1$ is aryl or 5- or 6-membered heteroaryl, each of which is optionally substituted with one or more substituents, each substituent independently being halogen (e.g., F, Cl, Br, or I), nitro, $C_1$-$C_4$ alkyl, $C_1$-$C_4$ hydroxyalkyl (e.g., $CH_2OH$), $OR_a$, or $N(R_aR_{a'})$, in which each $R_a$, independently, is H or $C_1$-$C_4$ alkyl and each $R_{a'}$, independently, is H or $C_1$-$C_4$ alkyl; $Ar^2$ is aryl or 5- or 6-membered heteroaryl, each of which is optionally substituted with one or more substituents, each substituent independently being halogen, cyano, nitro, $C_1$-$C_4$ alkyl, $C_1$-$C_4$ aminoalkyl (e.g., $CH_2NH_2$), $C_1$-$C_4$ hydroxyalkyl, $OR_b$, $N(R_bR_{b'})$, $C(O)$—$N(R_bR_{b'})$, or NH—$C(O)$—$N(R_bR_{b'})$, in which each $R_b$, independently, is H or $C_1$-$C_4$ alkyl and each $R_{b'}$, independently, is H or $C_1$-$C_4$ alkyl; $Ar^3$ is aryl or 5- or 6-membered heteroaryl, each of which is optionally substituted with one or more substituents, each substituent independently being halogen, $C_1$-$C_4$ alkyl, $C_1$-$C_4$ hydroxyalkyl, $OR_c$, or $N(R_cR_{c'})$, in which each $R_c$, independently, is H or $C_1$-$C_4$ alkyl and each $R_{c'}$, independently, is H or $C_1$-$C_4$ alkyl; each $R^1$, independently, is $C_1$-$C_4$ alkyl, $C_1$-$C_4$ aminoalkyl, $C_1$-$C_4$ hydroxyalkyl, $OR_d$, or $C(O)$—$N(R_dR_{d'})$, in which each $R_d$, independently, is H or $C_1$-$C_4$ alkyl and each $R_{d'}$, independently, is H or $C_1$-$C_4$ alkyl; $R^2$ is —$(CH_2)_n$—R, in which n is 0, 1, 2, or 3 and R is substituted or unsubstituted guanidino, aminoacyl (i.e., $C(O)NH_2$), $C_1$-$C_4$ alkylaminoacyl (e.g., $C(O)NHCH_3$), $OR_e$, $N(R_eR_{e'})$, NH—$C(O)$—$CH(NH_2)$—$(CH_2)_4$—$N(R_eR_{e'})$, NH—$C(O)$—$CH_2$—$(OCH_2CH_2)_2$—$N(R_eR_{e'})$, or 5-membered heterocycloalkyl optionally substituted with $C_1$-$C_4$ alkyl or $N(R_eR_{e'})$, in which each $R_e$, independently, is H or $C_1$-$C_4$ alkyl and each $R_{e'}$, independently, is H or $C_1$-$C_4$ alkyl; and each $R^3$, independently, is halogen, $C_1$-$C_4$ alkyl, or $OR_f$, in which each $R_f$, independently, is H or $C_1$-$C_4$ alkyl; with the provisos that, when n is 0, R is not amino or guanidino and that, when the amino acid residue bonded to $Ar^1C(O)$ is L-Val, $Ar^1$ is not unsubstituted phenyl.

The term "alkyl" refers to a saturated, linear or branched hydrocarbon moiety, such as —$CH_3$ or —$CH(CH_3)_2$. The term "cycloalkyl" refers to a saturated, cyclic hydrocarbon moiety, such as cyclohexyl. The term "heterocycloalkyl" refers to a saturated, cyclic moiety having at least one ring heteroatom (e.g., N, O, or S), such as 4-tetrahydropyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridinyl, pyrimidinyl, quinazolinyl, quinolyl, isoquinolyl and indolyl.

In some embodiments, the amino acid residue bonded to $Ar^1C(O)$ can be D-Val.

In some embodiments, $Ar^1$ can be phenyl, pyridinyl, oxazolyl, thiazolyl, imidazolyl, pyrimidinyl, pyrolyl, or triazolyl, each of which is optionally substituted with one or more substituents, such as F, Cl, $NO_2$, $CH_3$, $CH_2OH$, or $NH_2$.

In some embodiments, $Ar^2$ can be phenyl or pyridinyl, each of which is optionally substituted with one or more substituents, such as $CH_2NH_2$, $C(O)NH_2$, OH, CN, $CH_2OH$, $NH_2$, or NH—$C(O)$—$NH_2$.

In some embodiments, $Ar^3$ can be pyridinyl.

In some embodiments, $R^1$ can be OH, $C(O)NH_2$, or $CH_2NH_2$. In such embodiments, m in formula (I) can be 1.

In some embodiments, n in $R^2$ in formula (I) can be 0, 1, or 2.

In some embodiments, R can be $N(R_eR_{e'})$, NH—$C(O)$—$CH(NH_2)$—$(CH_2)_4$—$N(R_eR_{e'})$, NH—$C(O)$—$CH_2$—$(OCH_2CH_2)_2$—$N(R_eR_{e'})$, triazolyl optionally substituted with $NH_2$, or guanidino optionally substituted with CN or $CH_3$, in which each $R_e$, independently, is H or $C_1$-$C_3$ alkyl and each $R_{e'}$, independently, is H or $C_1$-$C_3$ alkyl. For example, R can be $NH_2$, $N(CH_3)_2$, $N(CH_2CH_3)_2$, $NH(CH(CH_3)_2)$, NH—$C(O)$—$CH(NH_2)$—$(CH_2)_4$—$N(CH_3)_2$, NH—$C(O)$—$CH_2$—$(OCH_2CH_2)_2$—$NH_2$, NH—$C(O)$—$CH_2$—$(OCH_2CH_2)_2$—$NH(CH(CH_3)_2)$, 3-amino-1,2,4-triazol-5-yl, or guanidino optionally substituted with CN or $CH_3$.

In some embodiments, p in formula (I) is 0.

Exemplary compounds of formula (I) (i.e., Compounds 1-70) include those listed in Table 1 below.

TABLE 1

| Cpd # | Sequence ID |
|---|---|
| 1 | Bz(4-F)-D-Val-Tyr-c(Cys-Arg-Asp-Val-Gly-Pro-Phe-Cys)-3Pal-$NH_2$ |
| 2 | Bz(4-F)-D-Val-Tyr-c(Cys-Arg-Asp-Val-Gly-Pro-3Pal-Cys)-3Pal-$NH_2$ |
| 3 | Picolinoyl-D-Val-Tyr-c(Cys-Arg-Asp-Val-Gly-Pro-3Pal-Cys)-3Pal-$NH_2$ |
| 4 | Bz(4-F)-D-Val-Tyr-c(Cys-Arg-Asp-Val-Gly-Dhp-Phe-Cys)-3Pal-$NH_2$ |
| 5 | Bz(4-F)-D-Val-Tyr-c(Cys-Arg-Asp-Val-Gly-Pro-Phe(3-$CH_2NH_2$)-Cys)-3Pal-$NH_2$ |

TABLE 1-continued

| Cpd # | Sequence ID |
|---|---|
| 6 | Bz(4-F)-D-Val-Tyr-c(Cys-Dpr-Asp-Val-Gly-Pro-Phe(3-Cbm)-Cys)-3Pal-NH$_2$ |
| 7 | Bz(4-F)-D-Val-Tyr-c(Cys-Dpr-Asp-Val-Gly-Pro-Tyr-Cys)-3Pal-NH$_2$ |
| 8 | Picolinoyl-D-Val-Tyr-c(Cys-Dab(Et2)-Asp-Val-Gly-Pro-Phe-Cys)-3Pal-NH$_2$ |
| 9 | Picolinoyl-D-Val-Tyr-c(Cys-Dab(iPr)-Asp-Val-Gly-Pro-Phe-Cys)-3Pal-NH$_2$ |
| 10 | Picolinoyl-D-Val-Tyr-c(Cys-Dpr(CO—CH$_2$—(O—(CH$_2$)$_2$)$_2$—NH$_2$)-Asp-Val-Gly-Pro-Phe-Cys)-3Pal-NH$_2$ |
| 11 | Oxazole-2-carbonyl-D-Val-Tyr-c(Cys-Arg-Asp-Val-Gly-Pro-3Pal-Cys)-3Pal-NH$_2$ |
| 12 | Picolinoyl(5-F)-D-Val-Tyr-c(Cys-Orn-Asp-Val-Gly-Pro-Phe-Cys)-3Pal-NH$_2$ |
| 13 | Picolinoyl(5-F)-D-Val-Tyr-c(Cys-Orn(CO—CH$_2$—(O—(CH$_2$)$_2$)$_2$—NH-iPr)-Asp-Val-Gly-Pro-Phe-Cys)-3Pal-NH$_2$ |
| 14 | Picolinoyl(5-F)-D-Val-Tyr-c(Cys-Orn(iPr)-Asp-Val-Gly-Pro-Phe-Cys)-3Pal-NH$_2$ |
| 15 | Bz(4-F)-D-Val-Phe(2-Cbm)-c(Cys-Arg-Asp-Val-Gly-Pro-Phe-Cys)-3Pal-NH$_2$ |
| 16 | Pyrimidine-4-carbonyl-D-Val-Tyr-c(Cys-Arg-Asp-Val-Gly-Pro-Phe-Cys)-3Pal-NH$_2$ |
| 17 | Picolinoyl(3-F)-D-Val-Tyr-c(Cys-Arg-Asp-Val-Gly-Pro-Phe-Cys)-3Pal-NH$_2$ |
| 18 | Picolinoyl(4-F)-D-Val-Tyr-c(Cys-Arg-Asp-Val-Gly-Pro-Phe-Cys)-3Pal-NH$_2$ |
| 19 | Bz(4-F)-D-Val-Tyr-c(Cys-norArg(CN)-Asp-Val-Gly-Pro-Phe-Cys)-3Pal-NH$_2$ |
| 20 | Bz(4-F)-D-Val-Tyr-c(Cys-Arg-Asp-Val-Gly-Pro-Phe(4-CH$_2$NH$_2$)-Cys)-3Pal-NH$_2$ |
| 21 | Bz(4-F)-D-Val-Tyr-c(Cys-Arg-Asp-Val-Gly-Pro-Phe(3-CN)-Cys)-3Pal-NH$_2$ |
| 22 | Bz(4-F)-D-Val-Phe(3-CH$_2$NH$_2$)-c(Cys-Arg-Asp-Val-Gly-Dhp-Tyr-Cys)-3Pal-NH$_2$ |
| 23 | Oxazole-2-carbonyl-D-Val-Phe(3-CH$_2$NH$_2$)-c(Cys-Arg-Asp-Val-Gly-Dhp-Phe(3-Cbm)-Cys)-3Pal-NH$_2$ |
| 24 | Picolinoyl-D-Val-Tyr-c(Cys-Orn(Et$_2$)-Asp-Val-Gly-Pro-Phe-Cys)-3Pal-NH$_2$ |
| 25 | Picolinoyl-D-Val-Tyr-c(Cys-Orn-Asp-Val-Gly-Pro-Phe(4-CH$_2$OH)-Cys)-3Pal-NH$_2$ |
| 26 | Picolinoyl-D-Val-Tyr-c(Cys-Arg(CN)-Asp-Val-Gly-Pro-Phe-Cys)-3Pal-NH$_2$ |
| 27 | Picolinoyl-D-Val-Tyr-c(Cys-Orn(Atz)-Asp-Val-Gly-Pro-Phe-Cys)-3Pal-NH$_2$ |
| 28 | Picolinoyl-D-Val-Tyr-c(Cys-Arg(Me)-Asp-Val-Gly-Pro-Phe-Cys)-3Pal-NH$_2$ |
| 29 | Picolinoyl(3-F)-D-Val-Tyr-c(Cys-Orn-Asp-Val-Gly-Pro-Phe(4-CH$_2$OH)-Cys)-3Pal-NH$_2$ |
| 30 | Oxazole-2-carbonyl-D-Val-Phe(2-Cbm)-c(Cys-Orn(iPr)-Asp-Val-Gly-Pro-Phe-Cys)-3Pal-NH$_2$ |
| 31 | Pyrimidine-4-carbonyl-D-Val-Phe(2-Cbm)-c(Cys-Arg-Asp-Val-Gly-Dhp-Phe(3-CH$_2$NH$_2$)-Cys)-3Pal-NH$_2$ |
| 32 | Picolinoyl(3-F)-D-Val-Phe(2-Cbm)-c(Cys-Arg-Asp-Val-Gly-Dhp-Phe(3-CH$_2$NH$_2$)-Cys)-3Pal-NH$_2$ |
| 33 | Thiazole-2-carbonyl-D-Val-Tyr-c(Cys-Arg-Asp-Val-Gly-Pro-Phe-Cys)-3Pal-NH$_2$ |
| 34 | Picolinoyl(3-Me)-D-Val-Tyr-c(Cys-Arg-Asp-Val-Gly-Pro-Phe-Cys)-3Pal-NH$_2$ |
| 35 | Picolinoyl(3,5-F2)-D-Val-Tyr-c(Cys-Arg-Asp-Val-Gly-Pro-Phe-Cys)-3Pal-NH$_2$ |
| 36 | Picolinoyl(3-NH$_2$)-D-Val-Tyr-c(Cys-Arg-Asp-Val-Gly-Pro-Phe-Cys)-3Pal-NH$_2$ |
| 37 | 1H-imidazole-5-carbonyl-D-Val-Tyr-c(Cys-Arg-Asp-Val-Gly-Pro-Phe-Cys)-3Pal-NH$_2$ |
| 38 | Picolinoyl(5-F)-D-Val-Phe(2-Cbm)-c(Cys-Orn(iPr)-Asp-Val-Gly-Dhp-3Pal-Cys)-3Pal-NH$_2$ |
| 39 | Picolinoyl(5-F)-D-Val-Phe(2-Cbm)-c(Cys-Orn(iPr)-Asp-Val-Gly-Pro-3Pal-Cys)-3Pal-NH$_2$ |
| 40 | Oxazole-2-carbonyl-D-Val-Phe(2-Cbm)-c(Cys-Orn(iPr)-Asp-Val-Gly-Pro-3Pal-Cys)-3Pal-NH$_2$ |
| 41 | Oxazole-2-carbonyl-D-Val-Phe(2-Cbm)-c(Cys-Lys(iPr)-Asp-Val-Gly-Pro-3Pal-Cys)-3Pal-NH$_2$ |
| 42 | Oxazole-2-carbonyl-D-Val-Phe(2-Cbm)-c(Cys-Dab(Atz)-Asp-Val-Gly-Pro-3Pal-Cys)-3Pal-NH$_2$ |
| 43 | Oxazole-2-carbonyl-D-Val-Phe(2-Cbm)-c(Cys-Orn(iPr)-Asp-Val-Gly-Dhp-Phe(3-CH$_2$NH$_2$)-Cys)-3Pal-NH$_2$ |
| 44 | Oxazole-2-carbonyl-D-Val-Tyr-c(Cys-Orn(Lys(Me$_2$))-Asp-Val-Gly-Pro-Phe-Cys)-3Pal-NH$_2$ |
| 45 | Pyrimidine-4-carbonyl-D-Val-Tyr-c(Cys-Orn(Lys(Me$_2$))-Asp-Val-Gly-Pro-Phe-Cys)-3Pal-NH$_2$ |
| 46 | Picolinoyl(3-F)-D-Val-Tyr-c(Cys-Orn(Me2)-Asp-Val-Gly-Pro-Phe-Cys)-3Pal-NH$_2$ |
| 47 | 1H-imidazole-4-carbonyl-D-Val-Tyr-c(Cys-Arg-Asp-Val-Gly-Pro-Phe-Cys)-3Pal-NH$_2$ |
| 48 | 1H-1,2,4-triazole-5-carbonyl(3-Me)-D-Val-Tyr-c(Cys-Arg-Asp-Val-Gly-Pro-Phe-Cys)-3Pal-NH$_2$ |
| 49 | 1H-pyrrole-2-carbonyl-D-Val-Tyr-c(Cys-Arg-Asp-Val-Gly-Pro-Phe-Cys)-3Pal-NH$_2$ |
| 50 | Picolinoyl(3-NO$_2$)-D-Val-Tyr-c(Cys-Arg-Asp-Val-Gly-Pro-Phe-Cys)-3Pal-NH$_2$ |
| 51 | Picolinoyl(3-Cl)-D-Val-Tyr-c(Cys-Arg-Asp-Val-Gly-Pro-Phe-Cys)-3Pal-NH$_2$ |
| 52 | Oxazole-2-carbonyl-D-Val-Phe(2-Cbm)-c(Cys-Orn(Atz)-Asp-Val-Gly-Pro-3Pal-Cys)-3Pal-NH$_2$ |
| 53 | 1H-1,2,4-triazole-5-carbonyl(3-Me)-D-Val-Tyr-c(Cys-Arg-Asp-Val-Gly-Pro-Phe(2-CH$_2$NH$_2$)-Cys)-3Pal-NH$_2$ |
| 54 | Picolinoyl-D-Val-Phe(2-Cbm)-c(Cys-Orn(iPr)-Asp-Val-Gly-Dhp-Phe(3-CH$_2$NH$_2$)-Cys)-3Pal-NH$_2$ |
| 55 | Picolinoyl-D-Val-Tyr-c(Cys-Orn(iPr)-Asp-Val-Gly-Pro-Phe(4-CH$_2$OH)-Cys)-3Pal-NH$_2$ |
| 56 | Picolinoyl(5-F)-D-Val-Tyr-c(Cys-Orn-Asp-Val-Gly-Pro-Phe(4-CH$_2$OH)-Cys)-3Pal-NH$_2$ |

TABLE 1-continued

| Cpd # | Sequence ID |
|---|---|
| 57 | Oxazole-2-carbonyl-D-Val-Phe(2-Cbm)-c(Cys-Orn(iPr)-Asp-Val-Gly-Dhp-Tyr-Cys)-3Pal-NH$_2$ |
| 58 | Oxazole-2-carbonyl-D-Val-Phe(2-Cbm)-c(Cys-Orn(iPr)-Asp-Val-Gly-Dhp-3Pal-Cys)-3Pal-NH$_2$ |
| 59 | Oxazole-2-carbonyl-D-Val-Phe(2-Cbm)-c(Cys-Orn(iPr)-Asp-Val-Gly-Dhp-4Aph-Cys)-3Pal-NH$_2$ |
| 60 | Oxazole-2-carbonyl-D-Val-Phe(2-Cbm)-c(Cys-Orn(iPr)-Asp-Val-Gly-Dhp-4Uph-Cys)-3Pal-NH$_2$ |
| 61 | Picolinoyl(5-F)-D-Val-Tyr-c(Cys-Orn(iPr)-Asp-Val-Gly-Pro-Phe(4-CH$_2$OH)-Cys)-3Pal-NH$_2$ |
| 62 | Picolinoyl(3,5-F2)-D-Val-Tyr-c(Cys-Orn(iPr)-Asp-Val-Gly-Pro-Phe-Cys)-3Pal-NH$_2$ |
| 63 | Picolinoyl(5-F)-D-Val-Phe(2-Cbm)-c(Cys-Orn(iPr)-Asp-Val-Gly-Dhp-Phe(4-CH$_2$OH)-Cys)-3Pal-NH$_2$ |
| 64 | Oxazole-2-carbonyl-D-Val-Phe(2-Cbm)-c(Cys-Orn(iPr)-Asp-Val-Gly-Pro-Phe(4-CH$_2$OH)-Cys)-3Pal-NH$_2$ |
| 65 | Oxazole-2-carbonyl-D-Val-Phe(2-Cbm)-c(Cys-Orn(iPr)-Asp-Val-Gly-Dhp-Phe(3-Cbm)-Cys)-3Pal-NH$_2$ |
| 66 | Picolinoyl(5-F)-D-Val-Phe(2-Cbm)-c(Cys-Orn(iPr)-Asp-Val-Gly-Dhp-Phe(2-Cbm)-Cys)-3Pal-NH$_2$ |
| 67 | Oxazole-2-carbonyl-D-Val-Tyr-c(Cys-Orn(iPr)-Asp-Val-Gly-Dhp-Phe(3-Cbm)-Cys)-3Pal-NH$_2$ |
| 68 | Picolinoyl(5-F)-D-Val-Tyr-c(Cys-Orn(iPr)-Asp-Val-Gly-Dhp-Phe(3-Cbm)-Cys)-3Pal-NH$_2$ |
| 69 | Picolinoyl-D-Val-Tyr-c(Cys-Orn(iPr)-Asp-Val-Gly-Dhp-Phe(4-CH$_2$OH)-Cys)-3Pal-NH$_2$ |
| 70 | Oxazole-2-carbonyl-D-Val-Tyr-c(Cys-Orn(iPr)-Asp-Val-Gly-Dhp-Phe(4-CH$_2$OH)-Cys)-3Pal-NH$_2$ |

Unless specified otherwise, the amino acid code in Table 1 refers to its L-isomer. For example, Orn refers to L-ornithine, 3Pal refers to 3-(3-Pyridyl)-L-alanine, Dhp refers to 3,4-dehydro-L-proline, and Phe(2-Cbm) refers to 3-(2-carbamoyl)phenyl-L-alanine.

Exemplary Compounds 1-70 are those of formula (I), in which m is 1, p is 0, Ar$^3$ is 3-pyridinyl, and A, Ar$^1$, Ar$^2$, R$^1$, n, and R are those shown in Table 2 below.

TABLE 2

| Cpd # | A | Ar$^1$ | Ar$^2$ | R$^1$ | n | R |
|---|---|---|---|---|---|---|
| 1 | single | 4-fluorophenyl | phenyl | 4-OH | 2 | guanidino |
| 2 | single | 4-fluorophenyl | 3-pyridinyl | 4-OH | 2 | guanidino |
| 3 | single | 2-pyridinyl | 3-pyridinyl | 4-OH | 2 | guanidino |
| 4 | double | 4-fluorophenyl | phenyl | 4-OH | 2 | guanidino |
| 5 | single | 4-fluorophenyl | 3-aminomethylphenyl | 4-OH | 2 | guanidino |
| 6 | single | 4-fluorophenyl | 3-carbamoylphenyl | 4-OH | 0 | NH$_2$ |
| 7 | single | 4-fluorophenyl | 4-hydroxyphenyl | 4-OH | 0 | NH$_2$ |
| 8 | single | 2-pyridinyl | phenyl | 4-OH | 1 | N(Et$_2$) |
| 9 | single | 2-pyridinyl | phenyl | 4-OH | 1 | NH—iPr |
| 10 | single | 2-pyridinyl | phenyl | 4-OH | 0 | NH—CO—CH$_2$—(O—(CH$_2$)$_2$)$_2$—NH$_2$ |
| 11 | single | 1,3-oxazol-2-yl | 3-pyridinyl | 4-OH | 2 | guanidino |
| 12 | single | 5-fluoropyridin-2-yl | phenyl | 4-OH | 2 | NH$_2$ |
| 13 | single | 5-fluoropyridin-2-yl | phenyl | 4-OH | 2 | NH—CO—CH$_2$—(O—(CH$_2$)$_2$)$_2$—NH—iPr |
| 14 | single | 5-fluoropyridin-2-yl | phenyl | 4-OH | 2 | NH—iPr |
| 15 | single | 4-fluorophenyl | phenyl | 2-C(O)—NH$_2$ | 2 | guanidino |
| 16 | single | pyrimidinyl | phenyl | 4-OH | 2 | guanidino |
| 17 | single | 3-fluoropyridin-2-yl | phenyl | 4-OH | 2 | guanidino |
| 18 | single | 4-fluoropyridin-2-yl | phenyl | 4-OH | 2 | guanidino |
| 19 | single | 4-fluorophenyl | phenyl | 4-OH | 1 | cyanoguanidino |
| 20 | single | 4-fluorophenyl | 4-aminomethylphenyl | 4-OH | 2 | guanidino |
| 21 | single | 4-fluorophenyl | 3-cyanophenyl | 4-OH | 2 | guanidino |
| 22 | double | 4-fluorophenyl | 4-hydroxyphenyl | 3-CH$_2$—NH$_2$ | 2 | guanidino |
| 23 | double | 1,3-oxazol-2-yl | 3-carbamoylphenyl | 3-CH$_2$—NH$_2$ | 2 | guanidino |
| 24 | single | 2-pyridinyl | phenyl | 4-OH | 2 | N(Et$_2$) |
| 25 | single | 2-pyridinyl | 4-hydroxymethylphenyl | 4-OH | 2 | NH$_2$ |
| 26 | single | 2-pyridinyl | phenyl | 4-OH | 2 | cyanoguanidino |
| 27 | single | 2-pyridinyl | phenyl | 4-OH | 2 | 3-amino-1,2,4-triazol-5-yl |
| 28 | single | 2-pyridinyl | phenyl | 4-OH | 2 | methylguanidino |
| 29 | single | 3-fluoropyridin-2-yl | 4-hydroxymethylphenyl | 4-OH | 2 | NH$_2$ |
| 30 | single | 1,3-oxazol-2-yl | phenyl | 2-C(O)—NH$_2$ | 2 | NH—iPr |
| 31 | double | pyrimidinyl | 3-aminomethylphenyl | 2-C(O)—NH$_2$ | 2 | guanidino |
| 32 | double | 3-fluoropyridin-2-yl | 3-aminomethylphenyl | 2-C(O)—NH$_2$ | 2 | guanidino |

TABLE 2-continued

| Cpd # | A | Ar¹ | Ar² | R¹ | n | R |
|---|---|---|---|---|---|---|
| 33 | single | 2-thiazolyl | phenyl | 4-OH | 2 | guanidino |
| 34 | single | 3-methylpyridin-2-yl | phenyl | 4-OH | 2 | guanidino |
| 35 | single | 3,5-difluoropyridin-2-yl | phenyl | 4-OH | 2 | guanidino |
| 36 | single | 3-aminopyridin-2-yl | phenyl | 4-OH | 2 | guanidino |
| 37 | single | 5-imidazolyl | phenyl | 4-OH | 2 | guanidino |
| 38 | double | 5-fluoropyridin-2-yl | 3-pyridinyl | 2-C(O)—NH$_2$ | 2 | NH—iPr |
| 39 | single | 5-fluoropyridin-2-yl | 3-pyridinyl | 2-C(O)—NH$_2$ | 2 | NH—iPr |
| 40 | single | 1,3-oxazol-2-yl | 3-pyridinyl | 2-C(O)—NH$_2$ | 2 | NH—iPr |
| 41 | single | 1,3-oxazol-2-yl | 3-pyridinyl | 2-C(O)—NH$_2$ | 3 | NH—iPr |
| 42 | single | 1,3-oxazol-2-yl | 3-pyridinyl | 2-C(O)—NH$_2$ | 2 | 3-amino-1,2,4-triazol-5-yl |
| 43 | double | 1,3-oxazol-2-yl | 3-aminomethylphenyl | 2-C(O)—NH$_2$ | 2 | NH—iPr |
| 44 | single | 1,3-oxazol-2-yl | phenyl | 4-OH | 2 | NH—C(O)—CH(NH$_2$)—(CH$_2$)$_4$—N(CH$_3$)$_2$ |
| 45 | single | pyrimidinyl | phenyl | 4-OH | 2 | NH—C(O)—CH(NH$_2$)—(CH$_2$)$_4$—N(CH$_3$)$_2$ |
| 46 | single | 3-fluoropyridin-2-yl | phenyl | 4-OH | 2 | NMe$_2$ |
| 47 | single | 5-imidazolyl | phenyl | 4-OH | 2 | guanidino |
| 48 | single | 1,2,4-triazol-5-yl | phenyl | 4-OH | 2 | guanidino |
| 49 | single | 2-pyrolyl | phenyl | 4-OH | 2 | guanidino |
| 50 | single | 3-nitropyridin-2-yl | phenyl | 4-OH | 2 | guanidino |
| 51 | single | 3-chloropyridin-2-yl | phenyl | 4-OH | 2 | guanidino |
| 52 | single | 1,3-oxazol-2-yl | 3-pyridinyl | 2-C(O)—NH$_2$ | 2 | 3-amino-1,2,4-triazol-5-yl |
| 53 | single | 1,2,4-triazol-5-yl | 2-aminomethylphenyl | 4-OH | 2 | guanidino |
| 54 | double | 2-pyridinyl | 3-aminomethylphenyl | 2-C(O)—NH$_2$ | 2 | NH—iPr |
| 55 | single | 2-pyridinyl | 4-hydroxymethylphenyl | 4-OH | 2 | NH—iPr |
| 56 | single | 5-fluoropyridin-2-yl | 4-hydroxymethylphenyl | 4-OH | 2 | NH$_2$ |
| 57 | double | 1,3-oxazol-2-yl | 4-hydroxyphenyl | 2-C(O)—NH$_2$ | 2 | NH—iPr |
| 58 | double | 1,3-oxazol-2-yl | 3-pyridinyl | 2-C(O)—NH$_2$ | 2 | NH—iPr |
| 59 | double | 1,3-oxazol-2-yl | 4-aminophenyl | 2-C(O)—NH$_2$ | 2 | NH—iPr |
| 60 | double | 1,3-oxazol-2-yl | 4-ureidophenyl | 2-C(O)—NH$_2$ | 2 | NH—iPr |
| 61 | single | 5-fluoropyridin-2-yl | 4-hydroxymethylphenyl | 4-OH | 2 | NH—iPr |
| 62 | single | 3,5-difluoropyridin-2-yl | 3-pyridinyl | 4-OH | 2 | NH—iPr |
| 63 | double | 5-fluoropyridin-2-yl | 3-pyridinyl | 2-C(O)—NH$_2$ | 2 | NH—iPr |
| 64 | single | 1,3-oxazol-2-yl | 4-hydroxymethylphenyl | 2-C(O)—NH$_2$ | 2 | NH—iPr |
| 65 | double | 1,3-oxazol-2-yl | 3-carbamoylphenyl | 2-C(O)—NH$_2$ | 2 | NH—iPr |
| 66 | double | 5-fluoropyridin-2-yl | 2-carbamoylphenyl | 2-C(O)—NH$_2$ | 2 | NH—iPr |
| 67 | double | 1,3-oxazol-2-yl | 3-carbamoylphenyl | 4-OH | 2 | NH—iPr |
| 68 | double | 5-fluoropyridin-2-yl | 3-carbamoylphenyl | 4-OH | 2 | NH—iPr |
| 69 | double | 2-pyridinyl | 4-hydroxymethylphenyl | 4-OH | 2 | NH—iPr |
| 70 | double | 1,3-oxazol-2-yl | 4-hydroxymethylphenyl | 4-OH | 2 | NH—iPr |

The compounds of formula (I) can be made by methods known in the art or methods described herein. Examples 1-5 below provide detailed descriptions of how compounds 1-70 were actually prepared.

This disclosure also features pharmaceutical compositions containing a therapeutically effective amount of at least one (e.g., two or more) of the CGRP antagonist peptides described herein (i.e., the compounds of formula (I)) or a pharmaceutically acceptable salt thereof as an active ingredient, as well as at least one pharmaceutically acceptable carrier (e.g., adjuvant or diluent). Examples of pharmaceutically acceptable salts include acid addition salts, e.g., salts formed by reaction with hydrohalogen acids (such as hydrochloric acid or hydrobromic acid), mineral acids (such as sulfuric acid, phosphoric acid and nitric acid), and aliphatic, alicyclic, aromatic or heterocyclic sulfonic or carboxylic acids (such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid, and naphthalenesulphonic acid).

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical carriers for delivery of an active CGRP antagonist peptide. Examples of other carriers include colloidal silicon oxide, magnesium stearate, cellulose, sodium lauryl sulfate, and D&C Yellow #10.

The pharmaceutical composition described herein can optionally include at least one further additive selected from a disintegrating agent, binder, lubricant, flavoring agent, preservative, colorant and any mixture thereof. Examples of such and other additives can be found in "Handbook of Pharmaceutical Excipients"; Ed. A. H. Kibbe, 3rd Ed., American Pharmaceutical Association, USA and Pharmaceutical Press UK, 2000.

The pharmaceutical composition described herein can be adapted for parenteral, oral, topical, nasal, rectal, buccal, or sublingual administration or for administration via the respiratory tract, e.g., in the form of an aerosol or an air-suspended fine powder. The term "parenteral" as used herein refers to subcutaneous, intracutaneous, intravenous, intramuscular, intraarticular, intraarterial, intrasynovial, intrasternal, intrathecal, intralesional, intraperitoneal, intraocular, intra-aural, or intracranial injection, as well as any suitable infusion technique. In some embodiments, the composition can be in the form of tablets, capsules, powders, microparticles, granules, syrups, suspensions, solutions, nasal spray, transdermal patches or suppositories.

In some embodiments, the pharmaceutical composition described herein can contain a CGRP antagonist peptide described herein that is dissolved in an aqueous solution. For example, the composition can include a sodium chloride aqueous solution (e.g., containing 0.9 wt % of sodium chloride) to serve as a diluent.

In addition, this disclosure features a method of using a CGRP antagonist peptide as outlined above for treating migraine or for the manufacture of a medicament for such a treatment. The method can include administering to a patient in need thereof an effective amount of the pharmaceutical composition described herein. "An effective amount" refers to the amount of the pharmaceutical composition that is required to confer a therapeutic effect on the treated subject. Effective doses will vary, as recognized by those skilled in the art, depending on the types of diseases treated, route of administration, excipient usage, and the possibility of co-usage with other therapeutic treatment.

As used herein, the terms "treatment," "treat," and "treating" refer to reversing, alleviating, delaying the onset of, or inhibiting the progress of, a migraine or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The typical dosage of the CGRP antagonist peptide described herein can vary within a wide range and will depend on various factors such as the individual needs of each patient and the route of administration. Exemplary daily dosages (e.g., for subcutaneous administration) can be at least about 0.5 mg (e.g., at least about 1 mg, at least about 5 mg, at least about 10 mg, or at least about 15 mg) and/or at most about 100 mg (e.g., at most about 75 mg, at most about 50 mg, at most about 20 mg, or at most about 15 mg) of a CGRP antagonist peptide. The skilled person or physician may consider relevant variations to this dosage range and practical implementations to accommodate the situation at hand.

In some embodiments, the pharmaceutical composition described herein can be administered once daily. In some embodiments, the pharmaceutical composition can be administered more than once daily (e.g., twice daily, three times daily, or four times daily).

The contents of all publications cited herein (e.g., patents, patent application publications, and articles) are hereby incorporated by reference in their entirety.

The following examples are illustrative and not intended to be limiting.

EXAMPLES

General Synthetic Methods
1. Amino Acid Derivatives

Amino acid derivatives were purchased from commercial providers (such as Aapptec, Chem Impex International, EMD Millipore, PPL, PepTech and Peptides International), except for Fmoc-Orn(iPr,Boc)-OH. Fmoc-Orn(iPr,Boc)-OH was prepared as follows:

50.0 g (105.8 mmol) of Fmoc-Orn(Boc)-OH was dissolved in 100 mL of dichloromethane (DCM). 100 mL of trifluoroacetic acid (TFA) was subsequently added. The reaction mixture was magnetically stirred for 1 hour and the solvents were evaporated. To remove excess TFA, the residue was reconstituted in DCM and evaporated several times. The oily residue was dissolved in 400 mL of MeOH and 100 mL of acetone, followed by 30 mL of acetic acid. The reaction mixture was vigorously stirred and 120.0 g (0.57 mol, 5.4 eq) of solid $NaBH(OAc)_3$ was added in 10 g portions until Fmoc-Orn-OH was consumed (about 2 hours, monitored by analytical HPLC). The solvents were then evaporated and the resulting solid residue was used in the next step without purification.

The residue obtained in the previous step was dissolved in 100 mL of water and the pH of the solution was adjusted to about 9.5 with solid $Na_2CO_3$. 100 mL of t-BuOH was subsequently added to the magnetically stirred reaction mixture. $Boc_2O$ (60.0 g, 275 mmol, 2.6 eq) in 100 mL of t-BuOH was then added portionwise over 10 hours. The pH of the reaction mixture was maintained at about 9.5 with the addition of saturated $Na_2CO_3$ (aq). After the last portion of $Boc_2O$ was added, the reaction mixture was stirred for 9 more hours. The reaction mixture was diluted with 1 L of water and extracted with 2×200 mL of hexane. The water phase was acidified with 2 M HCl and the product was extracted with diethyl ether (3×300 mL). The combined organic extracts were thoroughly washed with 2 M HCl (3×200 mL) and water, and were subsequently dried over anhydrous $MgSO_4$. The drying agent was filtered off and the solvent was evaporated. The resulting solid residue was treated with petroleum ether, decanted and dried in vacuo. The crystalline product was dissolved in 200 mL of t-BuOH and lyophilized. 41.8 g (84 mmol, 79.5% yield) of the lyophilized derivative was obtained.

2. Peptide Synthesis

Resins were purchased from commercial suppliers (e.g., PCAS BioMatrix Inc. and EMD Millipore). Carboxylic acids for the N-terminal acyl group introduction were obtained from AstaTech, ChemBridge Corp. Frontier Scientific, J&W Pharmalab, Oakwood Products and TCI America. All additional reagents, chemicals and solvents were purchased from Sigma-Aldrich and VWR.

The compounds described herein were synthesized by standard methods in solid phase peptide chemistry utilizing Fmoc methodology. The peptides were assembled either manually or automatically using a Tribute peptide synthesizer (Protein Technologies Inc., Tucson, Ariz.) or an Applied Biosystems 433A peptide synthesizer, or by combination of manual and automatic syntheses.

Preparative HPLC was performed on a Waters Prep LC System using a PrepPack cartridge Delta-Pack C18, 300 Å, 15 μm, 47×300 mm at a flow rate of 100 mL/min and/or on a Phenomenex Luna C18 column, 100 Å, 5 μm, 30×100 mm at a flow rate of 40 mL/min. Analytical reverse phase HPLC was performed on an Agilent Technologies 1200rr Series liquid chromatograph using an Agilent Zorbax C18 column, 1.8 μm, 4.6×110 mm at a flow rate of 1.5 mL/min. Final compound analyses were performed on an Agilent Technologies 1200 Series chromatograph by reverse phase HPLC on a Phenomenex Gemini 110 Å C18 column, 3 μm, 2×150 mm at a flow rate of 0.3 mL/min. Mass spectra were recorded on a MAT Finnigan LCQ electrospray mass spectrometer. Unless stated otherwise, all reactions were performed at room temperature. The following references provides further guidance on general experimental set up, as well as on the availability of required starting material and reagents: Kates, S. A., Albericio, F., Eds., Solid Phase Synthesis: A Practical Guide, Marcel Dekker, New York, Basel, 2000; Greene, T. W., Wuts, P. G. M., Protective Groups in Organic Synthesis, John Wiley Sons Inc., $2^{nd}$ Edition, 1991; Stewart, J. M., Young, J. D., Solid Phase Synthesis, Pierce Chemical Company, 1984; Bisello, et al., J. Biol. Chem. 1998, 273, 22498-22505; Merrifield, J. Am. Chem. Soc. 1963, 85, 2149-2154; and Chang and White P.

D., 'Fmoc Solid Phase Peptide Synthesis: a Practical Approach', Oxford University Press, Oxford, 2000.

The following protecting groups were utilized to protect the given amino acid side chain functional groups: Pbf (2,2,4,6,7-pentamethyldihydrobenzofuran-5-sulfonyl) for Arg; tBu (t-butyl) for Tyr and Asp; Boc (t-butoxycarbonyl) for Dab, Orn, Orn(iPr) and Lys; and Trt (trityl) for Cys.

Couplings of Fmoc-protected amino acids on the Tribute synthesizer were mediated with HBTU/NMM in DMF except for cysteine derivatives that were coupled with DIC/HOBt in DMF. Single cycles of 30-60 minutes with a 5-fold excess of activated Fmoc-protected amino acids were used during the synthesis. Removal of the Fmoc protecting group was monitored by UV. Multiple (up to 10 times, as needed) two-minute washes of the peptide resin with 20% piperidine in DMF were performed.

Cycle protocols specified by Applied Biosystems were used on the 433A synthesizer. Couplings were mediated with HATU/DIPEA or DIC/HOBt in DMF/NMP. Single couplings of 35-50 minutes with a 4-fold excess of activated Fmoc-protected amino acids were employed. Removal of the Fmoc protecting group was monitored by UV and was achieved by a single 20-minute wash with 20% piperidine/ NMP.

DIC/HOBt mediated couplings in DMF were employed for all amino acids in manual mode. Single cycles of at least 2 hours with up to 3-fold excess of activated Fmoc-protected amino acids were used during the synthesis. The completeness of couplings was assessed with nihidrine (Kaiser) test. Removal of the Fmoc protecting group was achieved with a single 30-minute wash of the peptide resin with 20% piperidine in DMF.

Upon completion of the peptide synthesis, the peptide resins were washed with DCM and dried in vacuo. The resins were treated with TFA containing variable amounts of $H_2O$ (up to 10%) and diisopropylsilane (TIS; up to 4%) for 2 hours to remove the side-chain protecting groups with concomitant cleavage of the peptide from the resin. The peptides were filtered, precipitated with diethyl ether and decanted. To obtain peptides with disulfide bridges, the precipitate was dissolved in neat TFA or AcOH and the solution was subsequently poured into 10% acetonitrile in water. In some cases an additional amount of acetonitrile was added to solubilize the substrate. The linear peptide was oxidized with 0.1M $I_2$ in MeOH or AcOH. The oxidizer solution was added dropwise until yellow color persisted. The excess of iodine was reduced with ascorbic acid. The pH was then adjusted to about 4 with concentrated ammonia. The obtained solution was loaded directly onto an HPLC prep column and eluted with a gradient of Component B shown in Table 3 below.

Each crude peptide was purified with Buffer T shown in Table 3. The fractions with a purity exceeding 90%, determined by reverse-phase analytical HPLC, were pooled and reloaded onto the column and eluted with Buffer T to provide trifluoroacetate salts. In some cases, an additional purification with Buffer C shown in Table 3 was performed. To obtain hydrochloride salts, the fractions from runs with Buffer T or C were reloaded onto the column and the column was washed with 3-5 volumes of 0.1 M sodium chloride in 1 mM HCl. The final product was eluted with Buffer H shown in Table 3. The fractions were pooled and lyophilized. The compounds thus prepared were typically found to be at least about 90% pure.

TABLE 3

Prep HPLC Buffer Compositions

| Buffer | Component A | Component B |
|---|---|---|
| C | 0.25M Triethylammonium Perchlorate, pH 2.3 | 60% acetonitrile, 40% Component A |
| T | 0.1% Trifluoroacetic acid (TFA) | 60% acetonitrile, 0.1% TFA |
| H | 1 mM HCl | 60% acetonitrile, 1 mM HCl |

Syntheses of certain exemplary compounds of formula (I) described herein are provided below.

Example 1: Synthesis of Compound 30

The peptide was assembled manually starting from 3.0 g (1.95 mmol) of Fmoc-Rink amide MBHA resin (EMD Millipore, catalog number 855003, 0.65 mmol/g). DIC/ HOBt mediated couplings in DMF were employed. Single cycles of at least 2 hours with up to 3-fold excess of activated Fmoc-protected amino acids were used during the synthesis. The completeness of couplings was assessed with nihidrine test. Removal of the Fmoc protecting group was achieved with a single 30-minute wash of the peptide resin with 20% piperidine in DMF. The following amino acid derivatives were used to assemble the resin-bound peptide: Fmoc-3Pal-OH, Fmoc-Cys(Trt)-OH, Fmoc-Phe-OH, Fmoc-Pro-OH, Fmoc-Gly-OH, Fmoc-Val-OH, Fmoc-Asp(tBu)-OH, Fmoc-Orn(iPr,Boc)-OH, Fmoc-Cys(Trt)-OH, Fmoc-Phe(2-Cbm)-OH and Fmoc-D-Val-OH. After the 1-11 peptide fragment was assembled, the resin was capped with oxazole-2-carboxylic acid/DIC/HOBt (4 eq), washed thoroughly with DCM and dried in vacuo. The crude linear peptide was cleaved from the resin with 50 mL of TFA/ $H_2O$/TIS 96:2:2 (v/v/v) for 2 hours. After the solvent was evaporated, the crude peptide was precipitated with diethyl ether and decanted. The precipitate was dissolved in 1 L of 1% aqueous TFA and oxidized with 0.1M $I_2$/MeOH. The oxidizer solution was added dropwise until yellow color persisted. The excess iodine was reduced with solid ascorbic acid. The pH was then adjusted to about 4 with concentrated ammonia. The obtained solution was loaded directly onto an HPLC prep column and purified with Buffer T. The fractions with purity >90%, determined by reverse-phase analytical HPLC, were pooled and reloaded onto the column. The column was equilibrated with 1 mM HCl, washed with 3 volumes of 0.1 mM NaCl in 1 mM HCl and the compound was eluted with Buffer H to provide hydrochloride salt. The fractions were pooled and lyophilized. 1009.8 mg (0.63 mmol, 32.3% overall based on 89.6% peptide content) of white peptide powder (Compound 30) was obtained.

The product purity was determined by analytical HPLC as 90.7%. The observed and calculated MS data (i.e., M+H) are provided in Table 4 below.

Example 2: Synthesis of Compound 40

The solid phase synthesis of this peptide was performed on the Tribute Peptide Synthesizer using Fmoc-strategy. The starting resin was 0.23 g (0.15 mmol) of Rink Amide MBHA resin (EMD Millipore, catalog number 855003, 100-200 mesh, 0.65 mmol/g). DIC/HOBt mediated couplings in DMF were employed for all amino acids except for the N-terminal oxazole-2-carboxylic acid that required HBTU/ NMM coupling method. Single cycles of 2 hours with 3-fold excess of activated Fmoc-protected amino acids were used during the synthesis. Fmoc protecting group was removed by treatment with 20% piperidine in DMF, 1×5 min and 1×25 min. The following amino acid derivatives were used consecutively to assemble the resin-bound peptide: Fmoc-3Pal-OH, Fmoc-Cys(Trt)-OH, Fmoc-3Pal-OH, Fmoc-Pro-OH, Fmoc-Gly-OH, Fmoc-Val-OH, Fmoc-Asp(tBu)-OH, Fmoc-Orn(iPr,Boc)-OH, Fmoc-Cys(Trt)-OH, Fmoc-Phe(2-Cbm)-OH and Fmoc-D-Val-OH. The N-terminal acyl group was introduced by treating the resin-bound (1-11) peptide fragment with pre-activated mixture of oxazole-2-carboxylic acid (0.5 mmol), HBTU (0.5 mmol), and DIEA (1.0 mmol) in DMF for 4 hours. The final assembled peptide resin was washed with DCM and dried in vacuo. The crude linear peptide was cleaved from the resin with 25 mL of TFA/H$_2$O/TIS (94:3:3, v/v/v) for 2.5 hours. The solvent was evaporated under vacuum and the crude peptide was precipitated with diethyl ether. The precipitate was collected by filtration and then dissolved in 400 mL of 0.1% TFA in 5% ACN and oxidized with 0.1M I$_2$/AcOH. The iodine solution was added dropwise until yellow color persisted. The excess of iodine was reduced with a saturated solution of ascorbic acid in water. The resulting solution was loaded directly onto a preparative HPLC column and purified with Buffer T. The fractions with purity>90%, determined by reverse-phase analytical HPLC, were pooled and freeze dried on a lyophilizer. 80.2 mg (45.0 μmol, 30% overall yield based on 80% estimated peptide content) of white peptide powder (Compound 40) was obtained.

The product purity was determined by analytical HPLC as 96.8%. The observed and calculated MS data (i.e., M+H) are provided in Table 4 below.

Example 3: Synthesis of Compound 62

The peptide was assembled manually starting from 3.0 g (1.77 mmol) of Rink amide MBHA resin (Novabiochem, catalog number 8.55003, 0.59 mmol/g), using high-temperature SPPS (75° C., Lauda E100 water bath, jacketed 50 mL SPPS reaction vessel). Single cycles of at least 15 minutes with up to 4-fold excess of preactivated Fmoc-protected amino acids (HOBt, DIC, no preactivation for Fmoc-Orn (iPr,Boc)-OH) were used during the synthesis. Fmoc protecting group was removed with a 2×5-minute wash of the peptide resin with 25% piperidine in DMF. The following amino acid derivatives were used to assemble the resin-bound peptide: Fmoc-3Pal-OH, Fmoc-Cys(Trt)-OH, Fmoc-Phe-OH, Fmoc-Pro-OH, Fmoc-Gly-OH, Fmoc-Val-OH, Fmoc-Asp(tBu)-OH, Fmoc-Orn(iPr,Boc)-OH, Fmoc-Cys(Trt)-OH, and Fmoc-D-Val-OH. After the 1-11 peptide fragment was assembled, the resin was capped with 3,5-difluoropicolinic acid/HATU/DIPEA (4 eq), washed thoroughly with MeOH, and dried in vacuo. The crude linear peptide was cleaved from the resin with 75 mL of TFA/H$_2$O/TIS 96:2:2 (v/v/v) for 2 hours. After the solvent was evaporated, the crude peptide was precipitated with diethyl ether and decanted. The precipitate was dissolved in 1 L of 10% MeCN in 0.5% aqueous TFA and oxidized with 0.05M I$_2$/AcOH. The oxidizer solution was added dropwise until yellow color persisted. The excess of iodine was reduced with 1 M ascorbic acid. The obtained solution was loaded directly onto an HPLC prep column and purified with modified Buffer T (Component A: 0.01% TFA, Component B: 95% acetonitrile in 0.01% TFA). The fractions with purity>95%, determined by reverse-phase analytical HPLC, were pooled and reloaded onto the column. The column was equilibrated with 1 mM HCl, washed with 3 volumes of 0.1 mM NaCl in 1 mM HCl and the compound was subsequently eluted with Buffer H to provide hydrochloride salt. The fractions were pooled and lyophilized. 583 mg (0.63 mmol, 20% overall based on 87.3% peptide content and 98.8% purity) of white peptide powder (Compound 62) was obtained.

The product purity was determined by analytical HPLC as 98.8%. The observed and calculated MS data (i.e., M+H) are provided in Table 4 below.

Example 4: Synthesis of Compound 65

The compound was assembled on solid phase by a combination of manual and automatic syntheses. First, the C-terminal tripeptide was synthesized manually starting from 7.3 g (3.5 mmol) of Fmoc-Rink amide Chem Matrix resin (Biotage, catalog number 7-600-1310-25, 0.48 mmol/g). HATU/DIPEA mediated couplings in DMF were employed for 3Pal and Phe(3-Cbm), and DIC/HOBt mediated coupling in DMF was used for Cys. Single cycles of at least 2 hours with up to 3-fold excess of activated Fmoc-protected amino acids were used during the synthesis. The completeness of couplings was assessed with nihidrine test. Removal of the Fmoc protecting group was achieved with 30% piperidine in DMF using two washes of 5 and 25 minutes, respectively. The following amino acid derivatives were used to assemble the resin-bound peptide: Fmoc-3Pal-OH, Fmoc-Cys(Trt)-OH and Fmoc-Phe(3-Cbm)-OH. The synthesis was continued on the 433A Synthesizer with one eighth (0.44 mmol) of the resin. HATU/DIPEA or DIC/HOBt (for Cys) mediated couplings in NMP/DMF were employed. Single cycles of at least 30 minutes with up to 5-fold excess of activated Fmoc-protected amino acids were used during the synthesis. Removal of the Fmoc protecting group was achieved with a single 30-minute wash of the peptide resin with 20% piperidine in NMP. The following amino acid derivatives were used to finish the assembly of the resin-bound peptide: Fmoc-Dhp-OH, Fmoc-Gly-OH, Fmoc-Val-OH, Fmoc-Asp(tBu)-OH, Fmoc-Orn(iPr,Boc)-OH, Fmoc-Cys(Trt)-OH, Fmoc-Phe(2-Cbm)-OH and Fmoc-D-Val-OH. After the 1-11 peptide fragment was assembled, the resin was capped manually with oxazole-2-carboxylic acid/HATU/DIPEA (4 eq), washed thoroughly with DCM, and dried in vacuo. The crude linear peptide was cleaved from the resin with 50 mL of TFA/H$_2$O/TIS 90:8:2 (v/v/v) for 2 hour. The solvent was evaporated and the crude peptide was precipitated with MTBA, centrifuged and decanted. The precipitate was dissolved in 15 mL of AcOH and poured into 250 mL of 10% (v/v) aqueous acetonitrile and oxidized with 0.1M I$_2$/MeOH. The oxidizer solution was added dropwise until yellow color persisted. The excess of iodine was reduced with solid ascorbic acid. The pH was then adjusted to about 4 with concentrated ammonia. The obtained solution was loaded directly onto an HPLC prep column and purified with Buffer T (see table above). The fractions with purity>90%, determined by reverse-phase analytical HPLC, were pooled and lyophilized. 116.2 mg (0.06 mmol, 14.1% overall based on 78.5% peptide content) of white peptide powder (Compound 65) was obtained.

The product purity was determined by analytical HPLC as 98.3%. The observed and calculated MS data (i.e., M+H) are provided in Table 4 below.

Example 5: Synthesis of Compounds 1-29, 31-39, 41-61, 63, 64, and 66-70

Compounds 1-29, 31-39, 41-61, 63, 64, and 66-70 were synthesized by using the methods described in Examples 1-4.

The observed and calculated MS data (i.e., M+H) of Compounds 1-70 are summarized in Table 4 below.

TABLE 4

| Compound No. | Calculated M + H | Observed M + H |
|---|---|---|
| 1 | 1425.6 | 1425.6 |
| 2 | 1426.6 | 1426.6 |
| 3 | 1408.6 | 1408.6 |
| 4 | 1423.6 | 1423.5 |
| 5 | 1454.6 | 1454.6 |
| 6 | 1398.5 | 1398.5 |
| 7 | 1371.5 | 1371.5 |
| 8 | 1408.6 | 1408.8 |
| 9 | 1394.6 | 1394.7 |
| 10 | 1628.7 | 1628.9 |
| 11 | 1398.6 | 1398.8 |
| 12 | 1384.6 | 1384.7 |
| 13 | 1571.7 | 1571.8 |
| 14 | 1426.6 | 1426.7 |
| 15 | 1452.6 | 1452.7 |
| 16 | 1409.6 | 1409.7 |
| 17 | 1426.6 | 1426.7 |
| 18 | 1426.6 | 1426.7 |
| 19 | 1436.6 | 1436.7 |
| 20 | 1454.6 | 1454.6 |
| 21 | 1450.6 | 1450.6 |
| 22 | 1452.6 | 1452.7 |
| 23 | 1452.6 | 1452.7 |
| 24 | 1422.6 | 1422.7 |
| 25 | 1396.6 | 1396.7 |
| 26 | 1433.6 | 1433.7 |
| 27 | 1448.6 | 1488.7 |
| 28 | 1422.6 | 1422.8 |
| 29 | 1414.6 | 1414.7 |
| 30 | 1425.6 | 1425.7 |
| 31 | 1463.6 | 1463.8 |
| 32 | 1480.6 | 1480.7 |
| 33 | 1414.5 | 1414.7 |
| 34 | 1422.6 | 1422.7 |
| 35 | 1444.6 | 1444.7 |
| 36 | 1423.6 | 1423.6 |
| 37 | 1397.6 | 1397.7 |
| 38 | 1452.6 | 1452.6 |
| 39 | 1454.6 | 1454.6 |
| 40 | 1426.6 | 1426.5 |
| 41 | 1440.6 | 1440.6 |
| 42 | 1452.6 | 1452.5 |
| 43 | 1452.6 | 1452.6 |
| 44 | 1512.7 | 1512.7 |
| 45 | 1523.7 | 1523.8 |
| 46 | 1412.6 | 1412.7 |
| 47 | 1397.6 | 1397.6 |
| 48 | 1412.6 | 1412.7 |
| 49 | 1396.6 | 1396.6 |
| 50 | 1453.6 | 1453.6 |
| 51 | 1442.6 | 1442.6 |
| 52 | 1466.6 | 1466.6 |
| 53 | 1441.6 | 1441.8 |
| 54 | 1462.6 | 1462.7 |
| 55 | 1438.6 | 1438.8 |
| 56 | 1414.6 | 1414.9 |
| 57 | 1439.6 | 1439.8 |
| 58 | 1424.6 | 1424.7 |
| 59 | 1438.6 | 1438.9 |
| 60 | 1481.6 | 1481.7 |
| 61 | 1456.6 | 1456.7 |
| 62 | 1444.6 | 1444.7 |
| 63 | 1481.6 | 1481.6 |
| 64 | 1455.6 | 1455.6 |
| 65 | 1466.6 | 1466.7 |
| 66 | 1494.6 | 1494.7 |
| 67 | 1439.6 | 1439.6 |
| 68 | 1467.6 | 1467.7 |
| 69 | 1436.6 | 1436.7 |
| 70 | 1426.6 | 1426.5 |

Example 6: CGRP Receptor Antagonist Activity Measured by cAMP Assay

CGRP receptor agonists increase intracellular cyclic adenosine mono-phosphate (cAMP). CGRP receptor antagonists can reduce the agonist effect. Antagonist activity was assessed by measurement of cyclic adenosine mono-phosphate (cAMP) using cell line stably expressing the hCGRP receptor (GeneBLAzer® CALCRL:RAMP1-CRE-bla Freestyle™ 293F, Invitrogen). hCGRP receptor expressing cells were maintained in DMEM high-glucose with GlutaMAX™ containing 10% (v/v) FBS, 0.1 mM NEAA, 25 mM HEPES, 5 ug/ml Blasticidin, 100 ug/ml Hygromycin, and 400 ug/ml Geneticin at 37° C. under 5% $CO_2$ in a humidified atmosphere. For cAMP measurement, cells were washed once with 5 ml 1×PBS, cell maintenance media was replaced with compound buffer ((CB): DMEM containing 0.1% BSA and 0.5 mM IBMX), and flasks were incubated for 1 hour at 37° C. under 5% $CO_2$ in a humidified atmosphere. Cells were removed from culture flasks using non-enzymatic cell dissociation buffer and harvested in CB. The reaction was performed in 384 well white small volume plates (Greiner) at a density of 10,000 cells/well. Cells were exposed to varying concentrations of antagonist compounds for 30 minutes in the presence of a fixed concentration of agonist (human α-CGRP). cAMP levels were measured using an HTRF (homogeneous time resolved fluorescence)-based competitive cAMP immunoassay (cAMP Dynamic 2 Kit, Cisbio), according to the manufacturer's instructions. The ratio of 665 nm and 615 nm time-resolved fluorescence readings (RFU) was calculated and a single-binding site, four parameter concentration response model: (MIN+((MAX−MIN)/(1+((EC50/x)^Hill)))), was used to perform non-linear regression analysis, generating the concentration response curve. Reported parameters include antagonist potency IC50 (the concentration causing half-maximal inhibition of the agonist response for antagonist compounds) and efficacy (% MPE: percent of the maximal possible effect).

Compounds 1-70 and three reference peptide compounds were tested in the above assay. The three references peptide compounds are: (1) Bz(4-F)-D-Val-Tyr-c(Cys-Agp-Asp-Val-Gly-Pro-Phe-Cys)-3Pal-$NH_2$ ("Reference Compound 1", i.e., Compound 36 in Yan et al., *J. Pept. Sci.* 2011, 17, 383-386), (2) Bz-D-Val-Tyr-c(Cys-Dpr-Asp-Val-Gly-Pro-Phe-Cys)-3Pal-$NH_2$ ("Reference Compound 2", Compound 33 in Yan et al., *J. Pept. Sci.* 2011, 17, 383-386), and (3) H-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-$NH_2$ ("Reference Compound 3", human α-CGRP(8-37)-$NH_2$ antagonist). The results are summarized in Table 5 below.

As shown in Table 5, Compounds 1-70 generally exhibited improved potency compared to Reference Compounds 1-3.

Example 7: AM2 Receptor Antagonist Activity Measured by cAMP Assay

Antagonist activity for the adrenomedullin receptor AM2 was determined using the method described in Example 6 above, with the following modifications. Instead of GeneBLAzer® CALCRL:RAMP1-CRE-bla Freestyle™ 293F cells, GeneBLAzer® CALCRL:RAMP3-CRE-bla Freestyle™ 293F cells were used to test activity at hAM2 receptors. The agonist was human adrenomedullin, instead of α-CGRP.

Compounds 1-70 and the three reference peptide compounds described in Example 6 were tested in this assay. The results are summarized in Table 5 below. In Table 5, the selectivity ratio for hCGRP over hAM2 is calculated as hCGRP-R $IC_{50}$/hAM2-R $IC_{50}$.

As shown in Table 5, a majority of Compounds 1-70 exhibited improved selectivity to hCGRP receptor over hAM2 receptor compared to Reference Compounds 1-3.

TABLE 5

| | hCGRP-R | | hAM2-R | | |
|---|---|---|---|---|---|
| Patent Cpd No. | IC50 Ave (nM) | Efficacy Antag (%) Ave | IC50 Ave (nM) | Efficacy Antag (%) Ave | selectivity ratio CGRP/AM2 |
| 1 | 0.14 | 100 | 52 | 101 | 362 |
| 2 | 0.08 | 100 | 45 | 100 | 555 |
| 3 | 0.12 | 100 | 35 | 101 | 285 |
| 4 | 0.17 | 100 | 29 | 113 | 172 |
| 5 | 0.13 | 100 | 26 | 99 | 192 |
| 6 | 0.17 | 100 | 101 | 113 | 612 |
| 7 | 0.13 | 100 | 43 | 100 | 334 |
| 8 | 0.09 | 100 | 30 | 100 | 347 |
| 9 | 0.15 | 100 | 51 | 106 | 351 |
| 10 | 0.19 | 100 | 114 | 107 | 589 |
| 11 | 0.13 | 100 | 25 | 108 | 198 |
| 12 | 0.11 | 100 | 18 | 100 | 172 |
| 13 | 0.10 | 100 | 26 | 100 | 249 |
| 14 | 0.12 | 100 | 20 | 100 | 167 |
| 15 | 0.10 | 100 | 58 | 99 | 610 |
| 16 | 0.07 | 100 | 6.8 | 101 | 93 |
| 17 | 0.05 | 100 | 7.1 | 100 | 148 |
| 18 | 0.16 | 100 | 8.1 | 98 | 52 |
| 19 | 0.19 | 100 | 48 | 100 | 248 |
| 20 | 0.18 | 100 | 54 | 100 | 309 |
| 21 | 0.13 | 100 | 33 | 99 | 258 |
| 22 | 0.19 | 100 | 33 | 101 | 175 |
| 23 | 0.05 | 100 | 21 | 100 | 400 |
| 24 | 0.11 | 100 | 128 | 98 | 1213 |
| 25 | 0.07 | 100 | 78 | 100 | 1071 |
| 26 | 0.06 | 100 | 38 | 100 | 636 |
| 27 | 0.15 | 100 | 119 | 98 | 765 |
| 28 | 0.07 | 100 | 68 | 99 | 1031 |
| 29 | 0.09 | 100 | 148 | 98 | 1699 |
| 30 | 0.11 | 100 | 700 | 98 | 6628 |
| 31 | 0.12 | 100 | 46 | 100 | 390 |
| 32 | 0.12 | 100 | 61 | 99 | 498 |
| 33 | 0.10 | 100 | 11 | 100 | 117 |
| 34 | 0.14 | 100 | 7.9 | 100 | 58 |
| 35 | 0.06 | 100 | 33 | 101 | 580 |
| 36 | 0.17 | 100 | 16 | 101 | 93 |
| 37 | 0.17 | 100 | 379 | 100 | 2295 |
| 38 | 0.06 | 100 | 87 | 101 | 1478 |
| 39 | 0.13 | 100 | 275 | 101 | 2125 |
| 40 | 0.09 | 100 | 980 | 98 | 10884 |
| 41 | 0.13 | 100 | 1020 | 97 | 8075 |
| 42 | 0.14 | 100 | 1225 | 97 | 9068 |
| 43 | 0.04 | 100 | 180 | 101 | 4693 |
| 44 | 0.17 | 100 | 114 | 100 | 668 |
| 45 | 0.18 | 100 | 198 | 98 | 1082 |
| 46 | 0.15 | 100 | 184 | 99 | 1189 |
| 47 | 0.16 | 100 | 232 | 99 | 1460 |
| 48 | 0.07 | 100 | 402 | 96 | 5610 |
| 49 | 0.19 | 100 | 89 | 99 | 461 |
| 50 | 0.18 | 100 | 8.1 | 99 | 46 |
| 51 | 0.14 | 100 | 13 | 100 | 92 |
| 52 | 0.15 | 100 | 770 | 97 | 5203 |
| 53 | 0.11 | 100 | 901 | 98 | 8130 |
| 54 | 0.17 | 100 | 150 | 99 | 898 |
| 55 | 0.18 | 100 | 137 | 100 | 746 |
| 56 | 0.17 | 100 | 55 | 100 | 328 |
| 57 | 0.12 | 100 | 624 | 99 | 5225 |
| 58 | 0.18 | 100 | 476 | 99 | 2588 |
| 59 | 0.17 | 100 | 467 | 99 | 2770 |
| 60 | 0.12 | 100 | 444 | 100 | 3759 |
| 61 | 0.10 | 100 | 89 | 100 | 934 |
| 62 | 0.14 | 100 | 85 | 100 | 592 |
| 63 | 0.10 | 101 | 85 | 98 | 848 |
| 64 | 0.12 | 101 | 1246 | 99 | 10594 |
| 65 | 0.06 | 101 | 318 | 100 | 5492 |
| 66 | 0.08 | 101 | 84 | 100 | 1027 |
| 67 | 0.09 | 101 | 103 | 99 | 1094 |
| 68 | 0.06 | 101 | 18 | 100 | 300 |
| 69 | 0.13 | 100 | 64 | 100 | 497 |
| 70 | 0.15 | 100 | 107 | 100 | 727 |
| Ref. Cpd. 1 | 0.20 | 100 | 42 | 98 | 210 |
| Ref. Cpd. 2 | 0.52 | 100 | 200 | 100 | 387 |
| Ref. Cpd. 3 | 4.1 | 100 | 35 | 101 | 9 |

Other embodiments are within the scope of the following claims.

What is claimed is:
1. A compound of formula (I) or a pharmaceutically acceptable salt thereof:

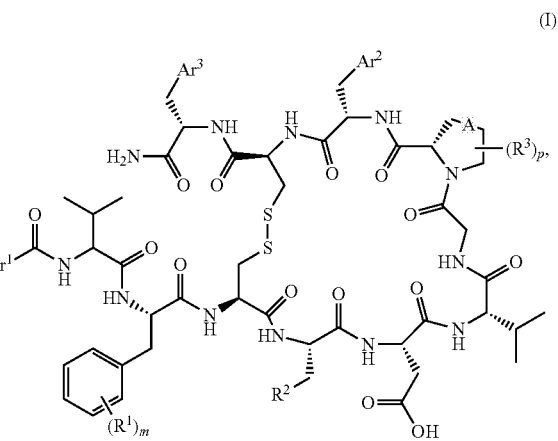

wherein
  m is 0, 1, 2, 3, 4, or 5;
  p is 0, 1, 2, or 3;
  A is single or double carbon-carbon bond;
  $Ar^1$ is aryl or 5- or 6-membered heteroaryl, each of which is optionally substituted with one or more substituents, each substituent independently being halogen, nitro, $C_1$-$C_4$ alkyl, $C_1$-$C_4$ hydroxyalkyl, $OR_a$, or $N(R_aR_{a'})$, in which each $R_a$, independently, is H or $C_1$-$C_4$ alkyl and each $R_{a'}$, independently, is H or $C_1$-$C_4$ alkyl;
  $Ar^2$ is aryl or 5- or 6-membered heteroaryl, each of which is optionally substituted with one or more substituents, each substituent independently being halogen, cyano, nitro, $C_1$-$C_4$ alkyl, $C_1$-$C_4$ aminoalkyl, $C_1$-$C_4$ hydroxyalkyl, $OR_b$, $N(R_bR_{b'})$, C(O)—N($R_bR_{b'}$), or NH—C(O)—N($R_bR_{b'}$), in which each $R_b$, independently, is H or $C_1$-$C_4$ alkyl and each $R_{b'}$, independently, is H or $C_1$-$C_4$ alkyl;
  $Ar^3$ is aryl or 5- or 6-membered heteroaryl, each of which is optionally substituted with one or more substituents, each substituent independently being halogen, $C_1$-$C_4$ alkyl, $C_1$-$C_4$ hydroxyalkyl, $OR_c$, or $N(R_cR_{c'})$, in which each $R_c$, independently, is H or $C_1$-$C_4$ alkyl and each $R_{c'}$, independently, is H or $C_1$-$C_4$ alkyl;

each independently, is $C_1$-$C_4$ alkyl, $C_1$-$C_4$ aminoalkyl, $C_1$-$C_4$ hydroxyalkyl, $OR_d$, or $C(O)$—$N(R_d R_{d'})$, in which each $R_d$, independently, is H or $C_1$-$C_4$ alkyl and each $R_{d'}$, independently, is H or $C_1$-$C_4$ alkyl;

$R^2$ is —$(CH_2)_n$—R, in which n is 0, 1, 2, or 3 and R is substituted or unsubstituted guanidino, aminoacyl, $C_1$-$C_4$ alkylaminoacyl, $OR_e$, $N(R_e R_{e'})$, NH—C(O)—CH(NH$_2$)—(CH$_2$)$_4$—$N(R_e R_{e'})$, NH—C(O)—CH$_2$—(OCH$_2$CH$_2$)$_2$—$N(R_e R_{e'})$, or 5-membered heterocycloalkyl optionally substituted with $C_1$-$C_4$ alkyl or $N(R_e R_{e'})$, in which each $R_e$, independently, is H or $C_1$-$C_4$ alkyl and each $R_{e'}$, independently, is H or $C_1$-$C_4$ alkyl; and each $R^3$, independently, is halogen, $C_1$-$C_4$ alkyl, or $OR_f$, in which each $R_f$, independently, is H or $C_1$-$C_4$ alkyl;

with the provisos that, when n is 0, R is not amino or guanidino and that, when the amino acid residue bonded to Ar$^1$C(O) is L-Val, Ar$^1$ is not unsubstituted phenyl.

2. The compound of claim 1, wherein Ar$^1$ is phenyl, pyridinyl, oxazolyl, thiazolyl, imidazolyl, pyrimidinyl, pyrolyl, or triazolyl, each of which is optionally substituted with one or more substituents, each substituent independently being F, Cl, NO$_2$, CH$_3$, CH$_2$OH, or NH$_2$.

3. The compound of claim 1, wherein Ar$^e$ is phenyl or pyridinyl, each of which is optionally substituted with one or more substituents, each substituent independently being CH$_2$NH$_2$, C(O)NH$_2$, OH, CN, CH$_2$OH, NH$_2$, or NH—C(O)—NH$_2$.

4. The compound of claim 1, wherein Ar$^a$ is pyridinyl.

5. The compound of claim 1, wherein m is 1.

6. The compound of claim 5, wherein $R^1$ is OH, C(O)NH$_2$, or CH$_2$NH$_2$.

7. The compound of claim 1, wherein n is 0, 1, or 2.

8. The compound of claim 1, wherein R is $N(R_e R_{e'})$, NH—C(O)—CH(NH$_2$)—(CH$_2$)$_4$—$N(R_e R_{e'})$, NH—C(O)—CH$_2$—(OCH$_2$CH$_2$)$_2$—$N(R_e R_{e'})$, triazolyl optionally substituted with NH$_2$, or guanidino optionally substituted with CN or CH$_3$, in which each $R_e$, independently, is H or $C_1$-$C_3$ alkyl and each $R_{e'}$, independently, is H or $C_1$-$C_3$ alkyl.

9. The compound of claim 1, wherein R is NH$_2$, N(CH$_3$)$_2$, N(CH$_2$CH$_3$)$_2$, NH(CH(CH$_3$)$_2$), NH—C(O)—CH(NH$_2$)—(CH$_2$)$_4$—N(CH$_3$)$_2$, NH—C(O)—CH$_2$—(OCH$_2$CH$_2$)$_2$—NH$_2$, NH—C(O)—CH$_2$—(OCH$_2$CH$_2$)$_2$—NH(CH(CH$_3$)$_2$), 3-amino-1,2,4-triazol-5-yl, or guanidino optionally substituted with CN or CH$_3$.

10. The compound of claim 1, wherein p is 0.

11. The compound of claim 1, wherein the compound is Oxazole-2-carbonyl-D-Val-Phe(2-Cbm)-c(Cys-Orn(iPr)-Asp-Val-Gly-Pro-Phe-Cys)-3Pal-NH$_2$.

12. The compound of claim 1, wherein the compound is
Picolinoyl-D-Val-Tyr-c(Cys-Dab(Et$_2$)-Asp-Val-Gly-Pro-Phe-Cys)-3Pal-NH$_2$;
Picolinoyl-D-Val-Tyr-c(Cys-Dab(iPr)-Asp-Val-Gly-Pro-Phe-Cys)-3Pal-NH$_2$;
Picolinoyl(5-F)-D-Val-Tyr-c(Cys-Orn(iPr)-Asp-Val-Gly-Pro-Phe-Cys)-3Pal-NH$_2$;
Picolinoyl-D-Val-Tyr-c(Cys-Orn(Et$_2$)-Asp-Val-Gly-Pro-Phe-Cys)-3Pal-NH$_2$;
Picolinoyl-D-Val-Tyr-c(Cys-Orn-Asp-Val-Gly-Pro-Phe(4-CH$_2$OH)-Cys)-3Pal-NH$_2$;
Picolinoyl(3,5-F2)-D-Val-Tyr-c(Cys-Arg-Asp-Val-Gly-Pro-Phe-Cys)-3Pal-NH$_2$;
Picolinoyl(5-F)-D-Val-Phe(2-Cbm)-c(Cys-Orn(iPr)-Asp-Val-Gly-Dhp-3Pal-Cys)-3Pal-NH$_2$;
Picolinoyl(5-F)-D-Val-Phe(2-Cbm)-c(Cys-Orn(iPr)-Asp-Val-Gly-Pro-3Pal-Cys)-3Pal-NH$_2$;
Oxazole-2-carbonyl-D-Val-Phe(2-Cbm)-c(Cys-Orn(iPr)-Asp-Val-Gly-Pro-3Pal-Cys)-3Pal-NH$_2$;
Oxazole-2-carbonyl-D-Val-Phe(2-Cbm)-c(Cys-Orn(iPr)-Asp-Val-Gly-Dhp-Phe(3-CH$_2$NH$_2$)-Cys)-3Pal-NH$_2$;
1H-1,2,4-triazole-5-carbonyl(3-Me)-D-Val-Tyr-c(Cys-Arg-Asp-Val-Gly-Pro-Phe(2-CH$_2$NH$_2$)-Cys)-3Pal-NH$_2$;
Oxazole-2-carbonyl-D-Val-Phe(2-Cbm)-c(Cys-Orn(iPr)-Asp-Val-Gly-Dhp-4Aph-Cys)-3Pal-NH$_2$;
Oxazole-2-carbonyl-D-Val-Phe(2-Cbm)-c(Cys-Orn(iPr)-Asp-Val-Gly-Dhp-4Uph-Cys)-3Pal-NH$_2$;
Picolinoyl(5-F)-D-Val-Tyr-c(Cys-Orn(iPr)-Asp-Val-Gly-Pro-Phe(4-CH$_2$OH)-Cys)-3Pal-NH$_2$;
Picolinoyl(3,5-F2)-D-Val-Tyr-c(Cys-Orn(iPr)-Asp-Val-Gly-Pro-Phe-Cys)-3Pal-NH$_2$;
Picolinoyl(5-F)-D-Val-Phe(2-Cbm)-c(Cys-Orn(iPr)-Asp-Val-Gly-Dhp-Phe(4-CH$_2$OH)-Cys)-3Pal-NH$_2$;
Oxazole-2-carbonyl-D-Val-Phe(2-Cbm)-c(Cys-Orn(iPr)-Asp-Val-Gly-Pro-Phe(4-CH$_2$OH)-Cys)-3Pal-NH$_2$;
Oxazole-2-carbonyl-D-Val-Phe(2-Cbm)-c(Cys-Orn(iPr)-Asp-Val-Gly-Dhp-Phe(3-Cbm)-Cys)-3Pal-NH$_2$;
Picolinoyl(5-F)-D-Val-Phe(2-Cbm)-c(Cys-Orn(iPr)-Asp-Val-Gly-Dhp-Phe(2-Cbm)-Cys)-3Pal-NH$_2$;
Oxazole-2-carbonyl-D-Val-Tyr-c(Cys-Orn(iPr)-Asp-Val-Gly-Dhp-Phe(3-Cbm)-Cys)-3Pal-NH$_2$;
Picolinoyl(5-F)-D-Val-Tyr-c(Cys-Orn(iPr)-Asp-Val-Gly-Dhp-Phe(3-Cbm)-Cys)-3Pal-NH$_2$; or
Picolinoyl-D-Val-Tyr-c(Cys-Orn(iPr)-Asp-Val-Gly-Dhp-Phe(4-CH$_2$OH)-Cys)-3Pal-NH$_2$.

13. A pharmaceutical composition, comprising the compound of claim 1 and a pharmaceutically acceptable carrier.

14. The pharmaceutical composition of claim 13, wherein the composition comprises an aqueous solution.

15. The pharmaceutical composition of claim 14, wherein the composition comprises a sodium chloride aqueous solution.

16. The pharmaceutical composition of claim 15, wherein the aqueous solution comprises about 0.9 wt % of sodium chloride.

17. A method of treating migraine, comprising administering to a patient in need thereof an effective amount of the pharmaceutical composition of claim 13.

* * * * *